US00PP26598P2

(12) United States Plant Patent
Nijland

(10) Patent No.: US PP26,598 P2
(45) Date of Patent: Apr. 12, 2016

(54) ***LONICERA* PLANT NAMED 'GOLDEN GLOW'**

(50) Latin Name: *Lonicera nitida*
Varietal Denomination: Golden Glow

(71) Applicant: Hendrik Johan Harmen Nijland, Harfsen (NL)

(72) Inventor: Hendrik Johan Harmen Nijland, Harfsen (NL)

(73) Assignee: Nijland Siergroen, Harfsen (NL)

( * ) Notice: Subject to any disclaimer, the term of this patent is extended or adjusted under 35 U.S.C. 154(b) by 15 days.

(21) Appl. No.: 14/121,360

(22) Filed: Aug. 25, 2014

(51) Int. Cl.
*A01H 5/02* (2006.01)

(52) U.S. Cl.
USPC ..... Plt./226

(58) Field of Classification Search
USPC ..... Plt./226
CPC ..... A01H 5/02; A01H 5/00
See application file for complete search history.

(56) References Cited

PUBLICATIONS http://www.newplants.nl/en/planten/l/lonicera-nitida-golden-glow/; 2013; 1 page.*

* cited by examiner

*Primary Examiner* — Kent L Bell
(74) *Attorney, Agent, or Firm* — Penny J. Aguirre

(57) ABSTRACT

A new cultivar of *Lonicera*, 'Golden Glow', that is characterized by its compact, well branched, and creeping plant habit, its foliage that is intense golden yellow in color that does not burn when grown under intense sun and hot temperatures, and its leaves that are ovate to narrow ovate in shape.

2 Drawing Sheets

Botanical classification: *Lonicera nitida.*
Variety denomination: 'Golden Glow'.

BACKGROUND OF THE INVENTION

The present invention relates to a new and distinct cultivar of *Lonicera nitida* and will be referred to hereafter by its cultivar name, 'Golden Glow'. 'Golden Glow' is a new cultivar of boxleaf honeysuckle, an evergreen shrub grown for use as an ornamental landscape plant.

The Inventor discovered the new cultivar in spring of 2008 as a naturally occurring branch mutation of *Lonicera nitida* 'Maigrün' (not patented) in a container block at his nursery in Harfsen, The Netherlands.

Asexual propagation of the new cultivar was first accomplished by the Inventor using softwood stem cuttings in 2008 in Harfsen, The Netherlands. Asexual propagation by softwood cuttings has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'Golden Glow' as a unique cultivar of *Lonicera.*

1. 'Golden Glow' exhibits a compact, well branched, and creeping plant habit.
2. 'Golden Glow' exhibits foliage that is intense golden yellow in color that does not burn when grown under intense sun and hot temperatures.
3. 'Golden Glow' exhibits leaves that are ovate to narrow ovate in shape.

The parent plant, 'Maigrün', differs from 'Golden Glow' in having foliage that is light green in color. In addition, 'Golden Glow' can be compared to *Lonicera nitida* cultivars 'Baggesen's Gold' and 'Lemon Beauty' (both not patented). 'Baggesen's Gold' is similar to 'Golden Glow' in foliage coloration, but differs from 'Golden Glow' in having an upright plant habit and in leaves that are smaller and round to broadly ovate in shape. 'Lemon Beauty' is similar to 'Golden Glow' in plant habit, but differs from 'Golden Glow' in having variegated leaves with green centers and golden yellow to cream colored margins.

BRIEF DESCRIPTION OF THE DRAWINGS

The accompanying colored photographs illustrate the overall appearance and distinct characteristics of the new *Lonicera*. The photographs were taken of a plant two years in age as field grown outdoors in Harfsen, The Netherlands and placed in a one-gallon container for the photographs.

The photograph in FIG. 1 provides a side view of 'Golden Glow' and illustrates its plant habit.

Figure 1:
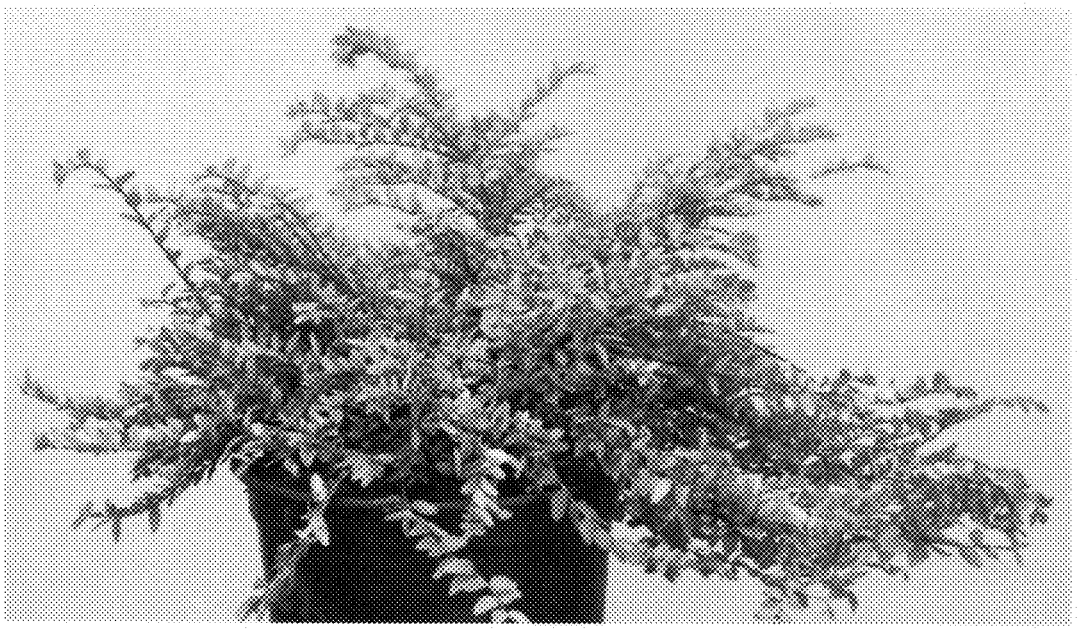
Figure 2:
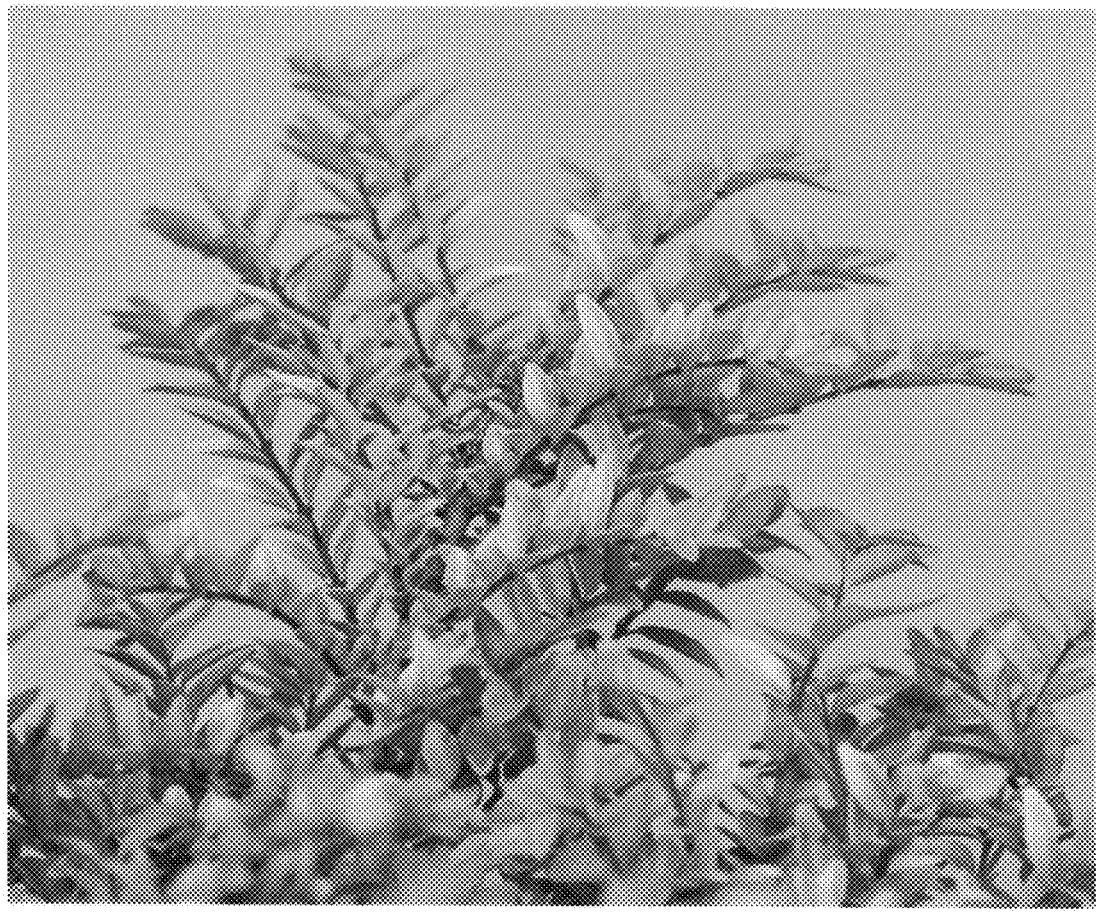

The photograph in FIG. 2 provides a close-up view of the foliage of 'Golden Glow'.

The colors in the photographs are as close as possible with the photographic and printing technology utilized and the color values cited in the detailed botanical description accurately describe the colors of the new *Lonicera.*

DETAILED BOTANICAL DESCRIPTION OF THE PLANT

The following is a detailed description of two year-old plants of 'Golden Glow' as field grown outdoors in Harfsen, The Netherlands. Phenotypic differences may be observed with variations in environmental, climatic, and cultural conditions. The color determination is in accordance with The 2007 R.H.S. Colour Chart of The Royal Horticultural Society, London, England, except where general color terms of ordinary dictionary significance are used.

General description:

*Plant type*.—Evergreen shrub.

*Plant habit*.—Compact, well branched, and creeping.

*Plant size*.—Average of 17.5 cm in height and 48.7 cm in spread.

*Hardiness*.—At least hardy to U.S.D.A. Zone 6.

*Diseases and pests*.—No particular resistance and susceptibility to diseases or pests have been observed to date.

*Root description*.—Fibrous.

*Propagation*.—Softwood stem cuttings.

*Growth rate*.—Moderately vigorous.

Stem description:

*Shape*.—Rounded.

*Stem color*.—New growth; upper side N186C, lower side 195A, mature bark; 199B to 199C.

*Stem quantity*.—Average of 15 main branches, each with an average of 24 lateral branches.

*Stem strength*.—Strong.

*Stem size*.—Main branch; average of 26 cm in length and 3.5 mm in diameter, lateral branches; 7.2 cm in length and 1 mm in diameter.

*Stem surface*.—Matte and moderately covered with dense short adpressed hairs; average of 0.5 mm in length and a color between 156A and 156D.

*Internode length*.—Average of 8 mm.

*Branching*.—Lateral branches at an average angle of 50° to main branches.

Foliage description:

*Leaf shape*.—Narrow ovate to ovate and slightly concave.

*Leaf division*.—Simple.

*Leaf base*.—Rounded to short attenuate.

*Leaf apex*.—Obtusely acute to obtuse.

*Leaf fragrance*.—None.

*Leaf venation*.—Pinnate, upper surface color; 154D, lower surface color; 145A.

*Leaf margins*.—Entire.

*Leaf arrangement*.—Alternate.

*Leaf attachment*.—Petiolate.

*Leaf surface*.—Glabrous and slightly leathery on both surfaces, upper side glossy, lower side slightly glossy and sparsely covered with short hairs on the main vein; 0.5 mm in length and 156D in color.

*Leaf size*.—Average of 1.2 cm in length and 6 mm in width.

*Leaf quantity*.—Average of 20 per branch (10 pairs).

*Leaf color*.—Young upper surface; N144A to N144D, young lower surface; 145A, mature upper surface; 9B with base N144C, mature lower surface; 12C with base 145B.

*Petioles*.—About 1.8 mm in length and 0.8 mm in width, 146D in color, glabrous surface.

*Stipules*.—None.

Inflorescence description: Flowers and seed production have not been observed to date.

It is claimed:

1. A new and distinct cultivar of *Lonicera* plant named 'Golden Glow' as herein illustrated and described.

* * * * *